(12) United States Patent
Lee

(10) Patent No.: US 11,661,578 B2
(45) Date of Patent: May 30, 2023

(54) CENTRIFUGAL PISTON AND CENTRIFUGAL DEVICE COMPRISING SAME

(71) Applicant: Jun Seok Lee, Busan (KR)

(72) Inventor: Jun Seok Lee, Busan (KR)

( * ) Notice: Subject to any disclaimer, the term of this patent is extended or adjusted under 35 U.S.C. 154(b) by 413 days.

(21) Appl. No.: 16/644,502

(22) PCT Filed: Sep. 4, 2018

(86) PCT No.: PCT/KR2018/010273
§ 371 (c)(1),
(2) Date: Mar. 5, 2020

(87) PCT Pub. No.: WO2019/050248
PCT Pub. Date: Mar. 14, 2019

(65) Prior Publication Data
US 2021/0087518 A1    Mar. 25, 2021

(30) Foreign Application Priority Data

Sep. 5, 2017 (KR) .................. 10-2017-0113330
Aug. 29, 2018 (KR) .................. 10-2018-0101990

(51) Int. Cl.
*C12M 1/00* (2006.01)
*B01D 21/26* (2006.01)
(Continued)

(52) U.S. Cl.
CPC ........... *C12M 45/05* (2013.01); *B01D 21/262* (2013.01); *B01L 3/5021* (2013.01); *B04B 5/0407* (2013.01); *B04B 11/04* (2013.01)

(58) Field of Classification Search
CPC ..... C12M 45/05; C12M 45/02; B01D 21/262; B01L 3/5021; B01L 2400/0409;
(Continued)

(56) References Cited

U.S. PATENT DOCUMENTS

| 3,887,464 A | 6/1975 | Ayres |
| 3,931,010 A | 1/1976 | Ayres et al. |
| 2008/0091147 A1* | 4/2008 | Lee .................. A61M 5/14566 604/190 |

(Continued)

FOREIGN PATENT DOCUMENTS

| KR | 20050122102 | 12/2005 |
| KR | 101137964 | 4/2012 |
| KR | 20120087125 | 8/2012 |

(Continued)

OTHER PUBLICATIONS

"International Search Report (Form PCT/ISA/210)" of PCT/KR2018/010273, dated Dec. 14, 2018, with English translation thereof, pp. 1-4.

*Primary Examiner* — Shuyi S. Liu
(74) *Attorney, Agent, or Firm* — JCIPRNET

(57) ABSTRACT

A centrifugal piston according to an embodiment comprises: a piston body defining a path which extends from the front of the piston to the rear of the piston, and through which substances at the front of the piston can move to the rear of the piston; and a valve disposed on the path and configured to selectively open or block the path, wherein, during centrifugation in which centrifugal force acts on the piston, the substances at the front of the piston are centrifuged while the valve is blocking the path, and, when an external force is applied to the piston while the centrifugal force does not act on the piston, the valve moves freely relative to the piston body, and when the valve opens the path, at least a portion of the substances at the front of the piston can move to the rear of the piston.

9 Claims, 8 Drawing Sheets

(51) Int. Cl.
  *B01L 3/00*   (2006.01)
  *B04B 5/04*   (2006.01)
  *B04B 11/04*  (2006.01)

(58) Field of Classification Search
  CPC ......... B01L 2400/0478; B01L 3/50215; B04B 5/0407; B04B 11/04; A61M 1/00; A61M 1/02; A61M 1/88; A61M 1/0272; A61M 1/029; A61M 1/81; A61M 2202/08
  USPC .............................. 604/190; 206/223; 494/16
  See application file for complete search history.

(56)            References Cited

U.S. PATENT DOCUMENTS

2011/0083978  A1*  4/2011  Lavi ................. A61B 5/150236
                                                              206/223
2019/0354020  A1   11/2019  Fan et al.

FOREIGN PATENT DOCUMENTS

| KR | 20120092332   |   | 8/2012  |
|----|---------------|---|---------|
| KR | 20120131925   |   | 12/2012 |
| KR | 20130091514   |   | 8/2013  |
| KR | 20140004890   |   | 1/2014  |
| KR | 20140017230   |   | 2/2014  |
| KR | 20140017230 A | * | 2/2014  |
| KR | 20140017948   |   | 2/2014  |
| KR | 20140040050   |   | 4/2014  |
| KR | 20150120797   |   | 10/2015 |
| KR | 101569175     |   | 11/2015 |
| KR | 20160125850   |   | 11/2016 |
| WO | 2015065011    |   | 5/2015  |

* cited by examiner

CENTRIFUGAL PISTON AND CENTRIFUGAL DEVICE COMPRISING SAME

CROSS-REFERENCE TO RELATED APPLICATION

This application is a 371 of international application of PCT application serial no. PCT/KR2018/010273, filed on Sep. 4, 2018, which claims the priority benefits of Korea application no. 10-2017-011333, filed on Sep. 5, 2017, and Korea application no. 10-2018-0101990, filed on Aug. 29, 2018. The entirety of each of the above-mentioned patent applications is hereby incorporated by reference herein and made a part of this specification.

TECHNICAL FIELD

The following description relates to a piston for centrifugation and a centrifugal separator including the same.

BACKGROUND ART

Adipose tissues obtained from objects, such as people, animals, and the like, by suction or incision contain a mixture of a large amount of oil and impurities, and centrifugation is performed on the adipose tissues to obtain pure fat. For example, Korean Patent Application Publication No. 10-2015-0120797 discloses a piston. According to the structure of the piston disclosed in this document, two bodies rotate relative to each other to selectively open or close a flow passage. Accordingly, whether a material passes through the flow passage is determined.

DISCLOSURE OF INVENTION

Technical Subject

An aspect provides a piston for centrifugation that interrupts or opens a passage through which a material passes, depending on whether a centrifugal force is applied or not, and a centrifugal separator including the piston.

Technical Solution

According to an example embodiment, there is provided a piston for centrifugation that includes a piston body having a passage defined therein and a valve disposed in the passage to selectively open or interrupt the passage, in which the passage extends from the front to the back of the piston, and materials ahead of the piston are movable to the rear of the piston through the passage. During the centrifugation that involves application of a centrifugal force to the piston, the materials ahead of the piston are centrifugally separated in a state in which the valve interrupts the passage, and when an external force is applied to the piston while a centrifugal force is not applied to the piston, at least a portion of the materials ahead of the piston are movable to the rear of the piston as the valve opens the passage while freely moving relative to the piston body.

The center of rotation of the centrifugal force may be located behind the piston body, the piston body may be located inside a container that receives the piston, and the piston body may apply pressure to the materials ahead of the piston while moving along the inside of the container depending on the external force.

The piston body may include a receiving portion to receive the valve and form a portion of the passage. The receiving portion may have an inner surface in a shape corresponding to at least a portion of the valve, and the passage may be interrupted when the valve is contact with the inner surface.

The passage may include a first path extending from one side of the piston body to the center of the piston body and a second path extending from the center of the piston body to the back of the piston body, and the second path may include a clearance formed between the valve and the inner surface when the valve is separated from the inner surface.

A portion of the receiving portion having the inner surface may have a decreasing width toward the front of the piston along a lengthwise direction of the piston body.

According to an example embodiment, there is provided a centrifugal separator that includes a piston including a piston body having a passage defined therein, the passage extending from the front to the back of the piston, a valve disposed in the passage, and a sealing member located on the passage and provided between the piston body and the valve, and a push rod to fix the valve to the piston body to interrupt the passage, the push rod being coupled with the piston body and the valve. The push rod is contact with the sealing member and interrupts communication of the passage together with the sealing member when the push rod is coupled with the piston body and the valve.

A portion of the push rod may be disposed inside the piston body to fill a space between the piston body and the valve and may form sealing of the passage together with the sealing member.

The sealing member may prevent separation of the valve from the piston body before the push rod is coupled with the piston body and the valve, and the sealing member may be elastically deformed before the push rod is separated from the piston body together with the valve after coupled with the piston body and the valve.

The piston may further include a groove, in which a portion of the sealing member is embedded in the piston body through the groove.

The valve may include a front valve part having a shape corresponding to an inner surface of the front of the piston body, a rear valve part having a shape corresponding to an inner surface of the back of the piston body, and a protruding component formed between the front valve part and the rear valve part and protruding toward the inner surface of the back of the piston body. The distance between the inner surface of the back of the piston body and the protruding component may be smaller than the distance from the inner surface of the back of the piston body to a portion of the sealing member facing toward the rear valve part.

According to an example embodiment, there is provided a centrifugation method for separating bio-materials using a piston for centrifugation. The piston includes a piston body having a passage defined therein and a valve disposed in the passage to open or interrupt the passage, in which the passage extends from the front to the back of the piston, and the bio-materials are movable through the passage. With respect to a container that receives the piston and the bio-materials, the bio-materials are located ahead of the piston body, and the center of rotation of a centrifugal force is located behind the piston body. The centrifugation method includes separating the bio-materials ahead of the piston body into layers in a direction away from the front of the piston body with respect to the center of rotation in a state in which the valve interrupts the passage while the centrifugal force is applied to the piston, releasing the centrifugal force applied to the piston, connecting a push rod to the piston body, and removing a bio-material farthest away from the piston body among the bio-materials from the container by applying pressure to the bio-materials by pushing the piston body in a direction toward the front of the piston body, moving a bio-material closest to the piston body among the bio-materials to the rear of the piston body through the passage in a state in which the valve opens the passage, by applying pressure to the bio-materials ahead of the piston by pushing the piston with the push rod in a state in which the connection of the push rod to the piston body is released, and obtaining at least one type of remaining bio-materials.

Effect of the Invention

The piston for centrifugation and the centrifugal separator including the same according to the example embodiments may obtain a desired material, by interrupting a flow of materials from the front to the back of the piston while a centrifugal force is applied, and allowing a specific material among the materials ahead of the piston to flow to the rear of the piston while a centrifugal force is not applied.

Effects of the piston for centrifugation and the centrifugal separator including the same according to the example embodiments are not limited to the aforementioned effects, and any other effects not mentioned herein will be clearly understood from the following description by those skilled in the art to which the present invention pertains.

BEST MODE FOR CARRYING OUT THE INVENTION

Figure 1:
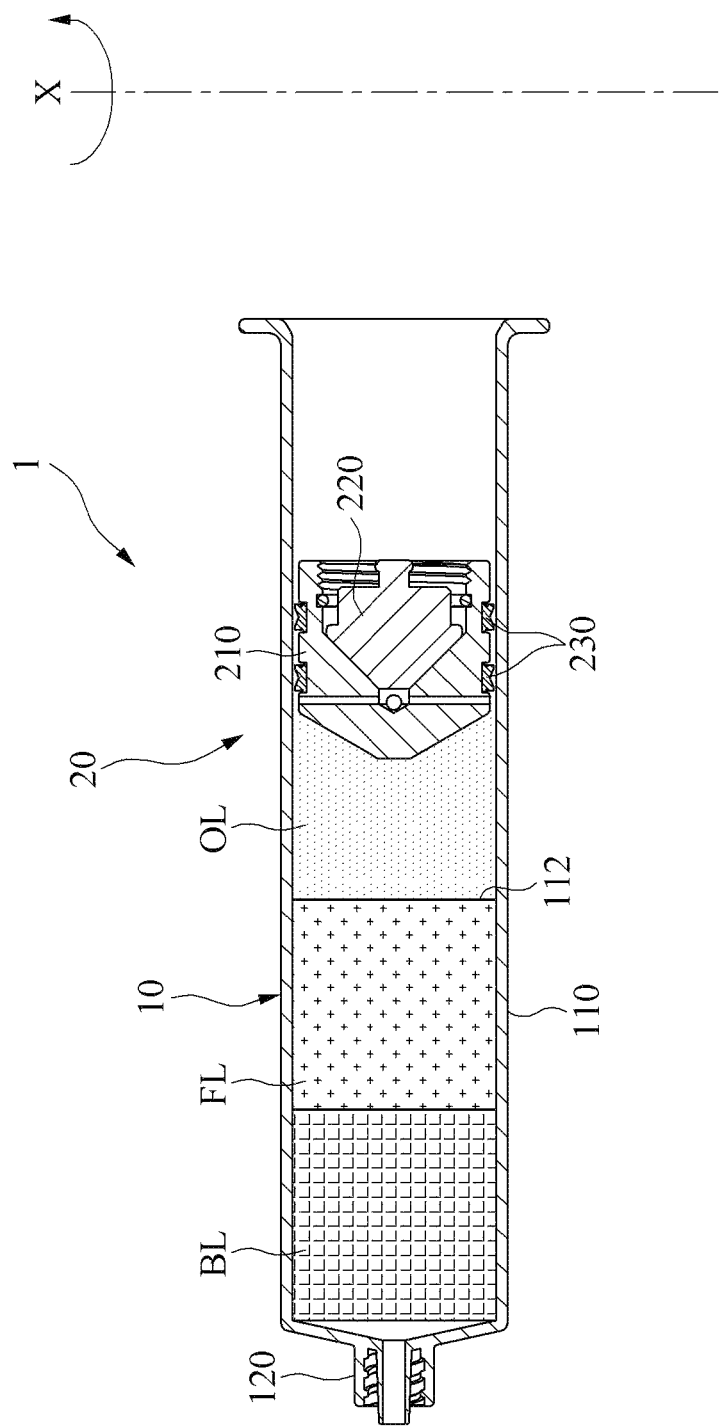
FIG. 1 is a cross-sectional view schematically illustrating centrifugation performed by a centrifugal separator according to an example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present invention.

In describing components of the example embodiments according to the present invention, terms such as first, second, "A", "B", (a), (b), and the like may be used. These terms are merely intended to distinguish one component from another component, and the terms do not limit the nature, sequence or order of the components. When a component is described as "connected", "coupled", or "linked" to another component, this may mean the components are not only directly "connected", "coupled", or "linked", but also are indirectly "connected", "coupled", or "linked" via a third component.

A component, which has the same common function as a component included in any one example embodiment, will be described using the same name in other example embodiments. Unless otherwise stated, the description set forth in any one example embodiment may be applicable to other example embodiments, and a detailed description will be omitted in an overlapping range.

The term "objects" used herein may be used as a concept including living things such as people, animals, and the like.

The term "biological tissues" used herein refers to tissues obtained from the objects. For example, the biological tissues may include adipose tissues. The biological tissues may be obtained from the objects by a method such as suction or incision.

The term "the front of a piston" used herein refers to an upstream side with respect to a flow stream of a bio-material passing through the piston, and the term "the back of the piston" refers to a downstream side with respect to the flow stream of the bio-material passing through the piston.

Figure 2:
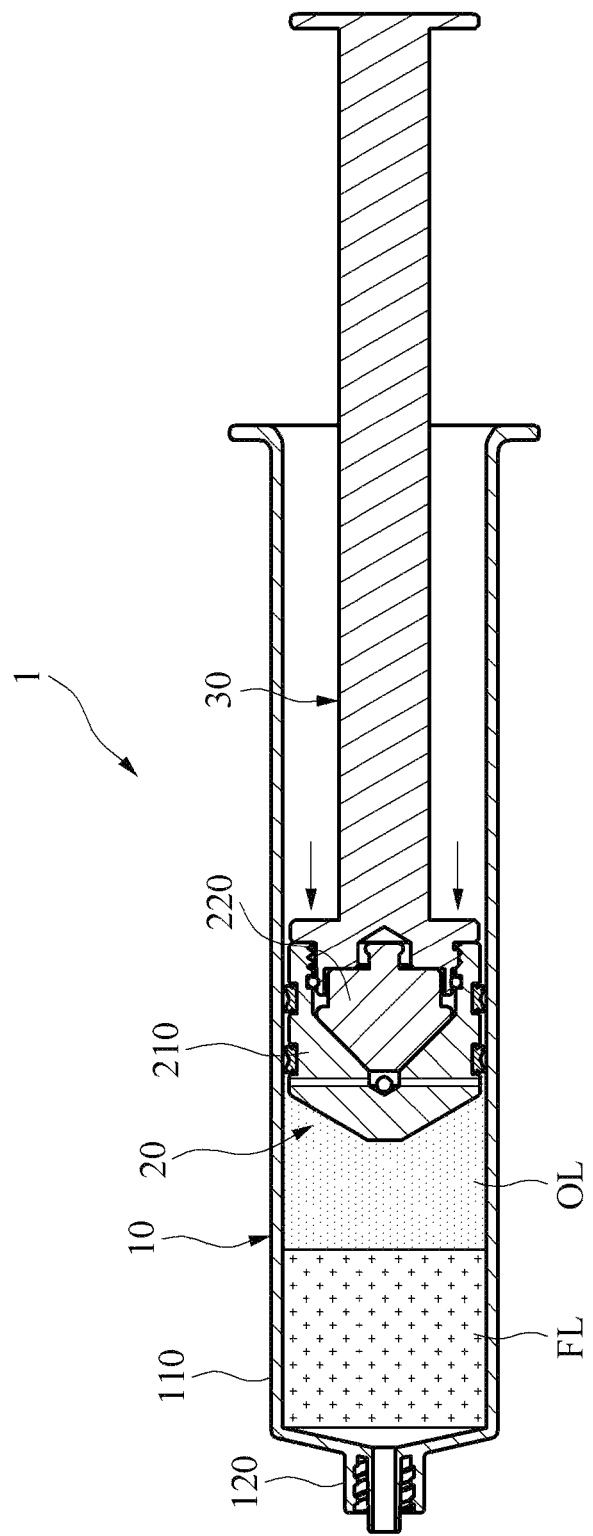
FIG. 2 is a cross-sectional view schematically illustrating removal of a bio-material from a distal region ahead of a piston after centrifugation is performed by a centrifugal separator according to an example embodiment.
Figure 3:
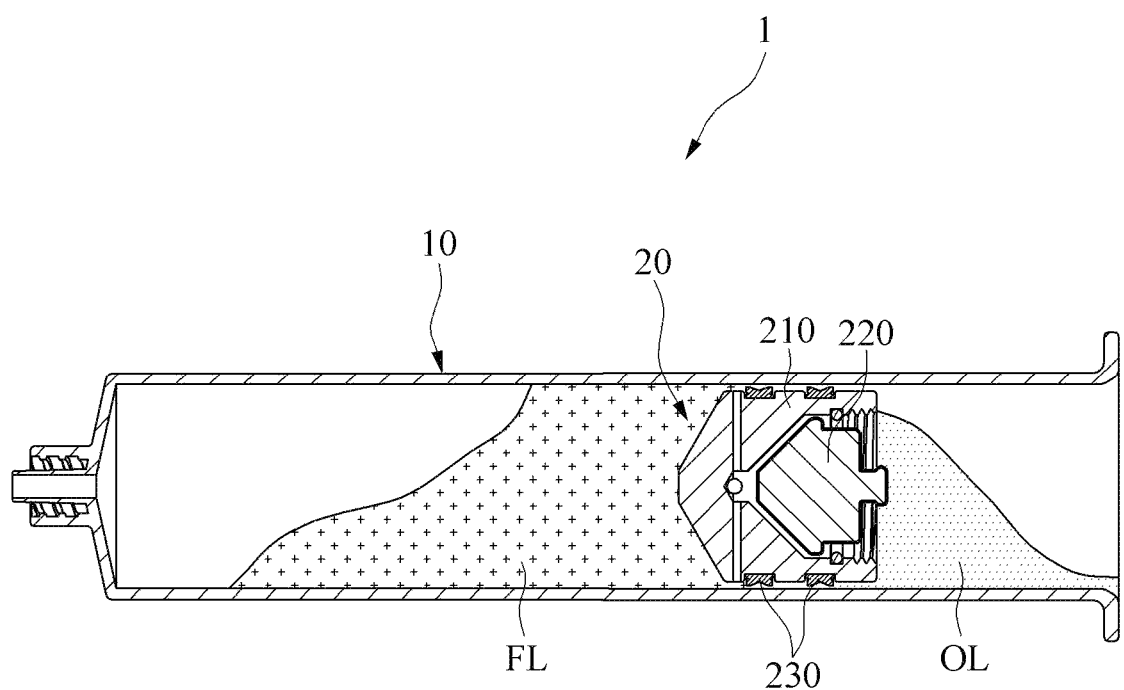
FIG. 3 is a cross-sectional view schematically illustrating removal of a bio-material from a proximal region ahead of a piston after centrifugation is performed by a centrifugal separator according to an example embodiment.

FIG. 1 is a cross-sectional view schematically illustrating centrifugation performed by a centrifugal separator according to an example embodiment. FIG. 2 is a cross-sectional view schematically illustrating removal of a bio-material from a distal region ahead of a piston after the centrifugation is performed by the centrifugal separator according to the example embodiment. FIG. 3 is a cross-sectional view schematically illustrating removal of a bio-material from a proximal region ahead of the piston after the centrifugation is performed by the centrifugal separator according to the example embodiment.

Referring to FIGS. 1 to 3, the centrifugal separator 1 according to the example embodiment is configured to obtain a desired bio-material FL by centrifugally separating bio-materials BL, FL, and OL constituting biological tissue and thereafter removing some bio-materials BL and OL by a predetermined method. Hereinafter, it will be exemplified that the centrifugal separator 1 centrifugally separates adipose tissue that is one of biological tissues. However, example embodiments are not necessarily limited thereto.

The centrifugal separator 1 may include a container 10, a piston 20, and a push rod 30.

The container 10 is configured to receive adipose tissue, the piston 20, and the push rod 30. The container 10 includes a main body 110 having a substantially cylindrical shape. For example, the main body 110 may be a syringe. The main body 110 has, at the front thereof (at a left end of the main body 110 with respect to FIG. 1), an outlet 120 through which a material constituting the adipose tissue escapes from the main body 110. The main body 110 has, at the back thereof (at a right end of the main body 110 with respect to FIG. 1), an opening through which the adipose tissue, the piston 20, and the push rod 30 are inserted into the main body 110.

The piston 20 is configured to move in the main body 110. The piston 20 may include a piston body 210, a valve 220, and one or more outer sealing members 230.

The piston body 210 is configured to move in the main body 110. A passage extending from the front to the back of the piston 20 is defined in the piston body 210. The piston body 210 may have a substantially cylindrical shape.

The valve 220 is disposed in the passage defined in the piston body 210 and is configured to open or interrupt the passage. For example, the valve 220 may selectively open or interrupt the passage as a centrifugal force is applied. The valve 220 may be received in the piston body 210 and may freely move in the piston body 210.

The outer sealing members 230 are coupled to the outside of the piston body 210 and are configured to seal between the piston body 210 and the main body 110. The outer sealing members 230 are configured to make contact with an inner surface 112 of the main body 110. The piston body 210 may be fixed to the main body 110 in any location of the main body 110 by a frictional force between the outer sealing members 230 and the inner surface 112 of the main body 110.

The push rod 30 is configured to be coupled with the piston body 210 and the valve 220. In the state of being coupled with the piston body 210 and the valve 220, the push rod 30 may push the piston 20 toward the front of the main body 110 (e.g., by an external force of a user). At this time, some materials of the adipose tissue ahead of the piston 20 may escape from the main body 110 through the outlet 120. Furthermore, in the state of being coupled with the valve 220, the push rod 30 may be separated from the piston body 210. At this time, the valve 220, together with the push rod 30, may be separated from the piston body 210.

An axis of rotation X that is the center of rotation for centrifugation may be located behind the main body 110 and behind the piston body 210 (on a right side with respect to FIG. 1). In this case, inside the main body 110, blood, fluid, pure fat, oil, and the like that constitute the adipose tissue are located ahead of the piston body 210 (on a left side with respect to FIG. 1), and the piston 20 is located next.

Referring to FIG. 1, when centrifugation is performed, the adipose tissue located ahead of the piston 20 is separated into the oil layer OL, the fat layer FL, blood, and the fluid layer BL in sequence from a proximal region to a distal region ahead of the piston 20 according to specific gravity. Meanwhile, the piston body 210 and the valve 220 move in a direction away from the axis of rotation X. In this process, the piston body 210 is fixed to the main body 110 by friction between the outer sealing members 230 coupled to the outside of the piston body 210 and the inner surface 112 of the main body 110, and the valve 220 interrupts the passage defined in the piston body 210 while freely moving in the piston body 210. Because the valve 220 interrupts the passage defined in the piston body 210 during the centrifugation that involves the application of a centrifugal force, the oil layer OL, the fat layer FL, the blood, and the fluid layer BL ahead of the piston 20 cannot move through the passage. Some of the materials in the fat layer FL have a very small size and therefore may flow through the passage together with the oil in the oil layer OL in the process in which the centrifugation is performed. Accordingly, in the process in which the centrifugation is performed, the valve 220 may interrupt the passage in the piston 210, thereby preventing some materials in the fat layer FL, which are materials that a user generally wants, from moving from the front to the back of the piston 20 together with the oil in the oil layer OL.

Referring to FIG. 2, the push rod 30 may be coupled to the piston body 210 and the valve 220 in a state in which the centrifugation is completed, with no centrifugal force applied to the piston 20. At this time, the valve 220 remains interrupting the passage defined in the piston body 210. When the outlet 120 of the main body 110 is opened and an external force is applied to the push rod 30 in a direction toward the front of the main body 110, the blood located in the distal region ahead of the piston 20 and the blood and fluid in the fluid layer BL are discarded outside the main body 110 through the outlet 120.

Referring to FIG. 3, in the state in which the centrifugation is completed and the blood and the fluid layer BL are removed from the container 10, the push rod 30 may be separated from the piston body 210 and the valve 220. Because no centrifugal force is applied to the piston 20, the valve 220 may open the passage defined in the piston body 210 while freely moving in the piston body 210. At this time, the oil in the oil layer OL located in the proximal region ahead of the piston 20 may flow from the front to the back of the piston 20 through the passage defined in the piston body 210. The oil of the oil layer OL that flows to the back of the piston 20 is removed from the container 10, and when the piston 20 is removed from the container 10, the pure fat in the fat layer FL is obtained.

Figure 4:
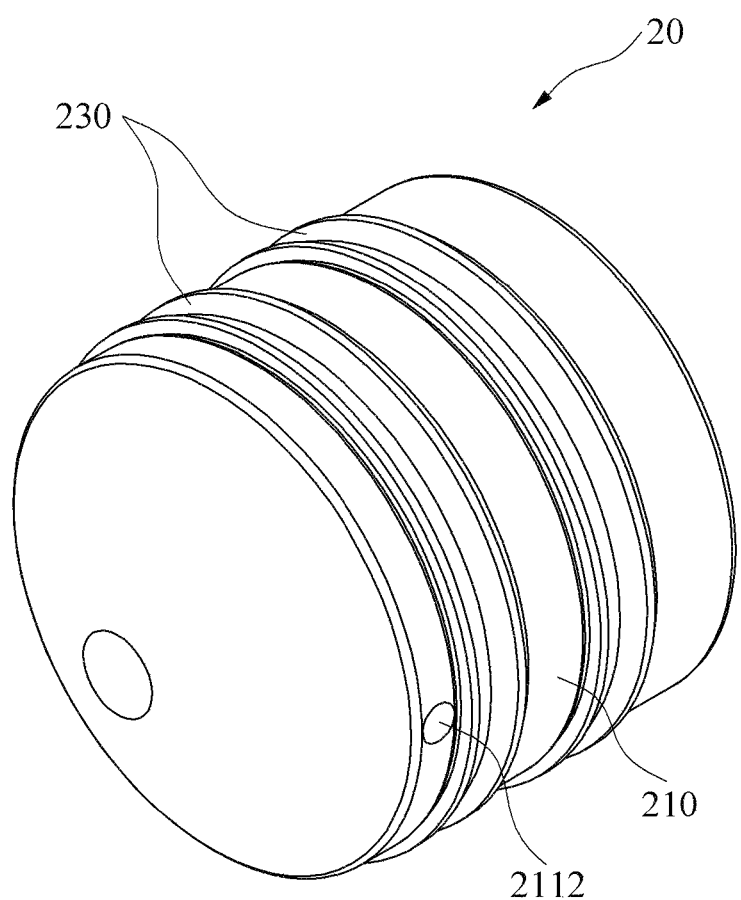
FIG. 4 is a perspective view schematically illustrating a piston according to an example embodiment.
Figure 5:
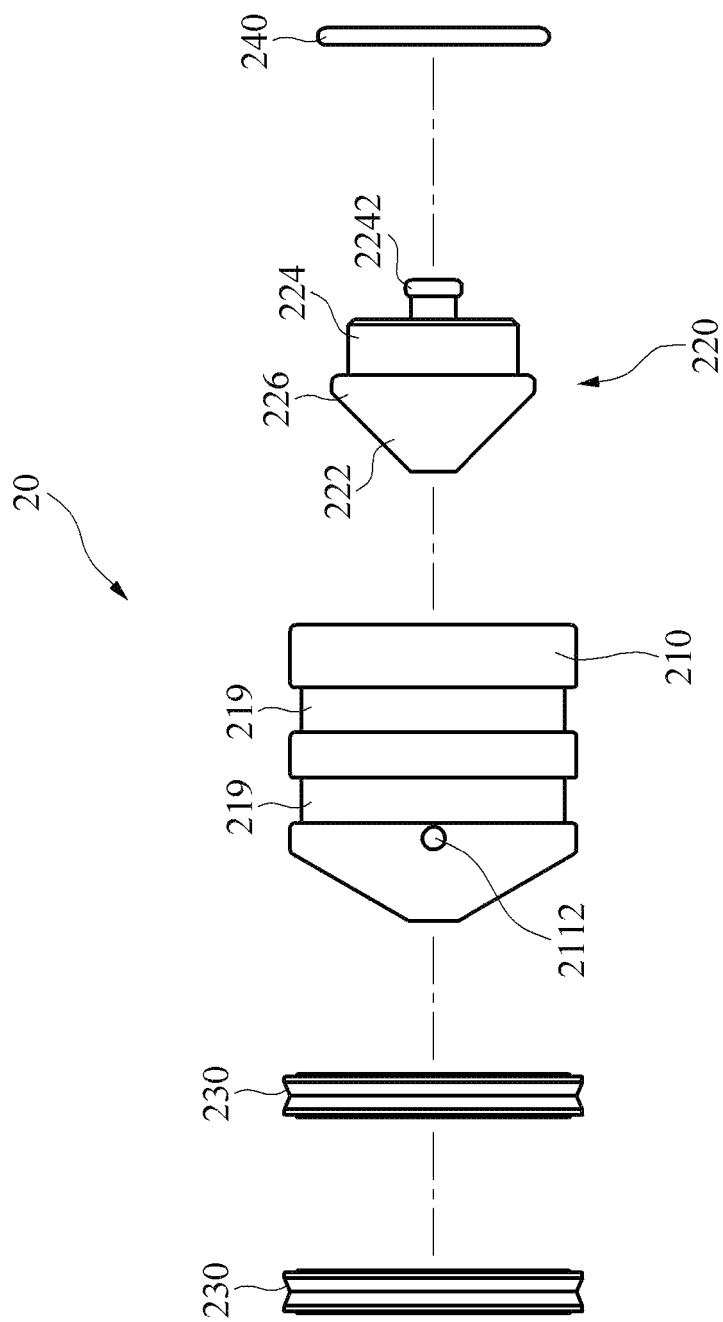
FIG. 5 is an exploded side view schematically illustrating a piston according to an example embodiment.

FIG. 4 is a perspective view schematically illustrating the piston according to an example embodiment, and FIG. 5 is an exploded side view schematically illustrating the piston according to the example embodiment.

Figure 6:
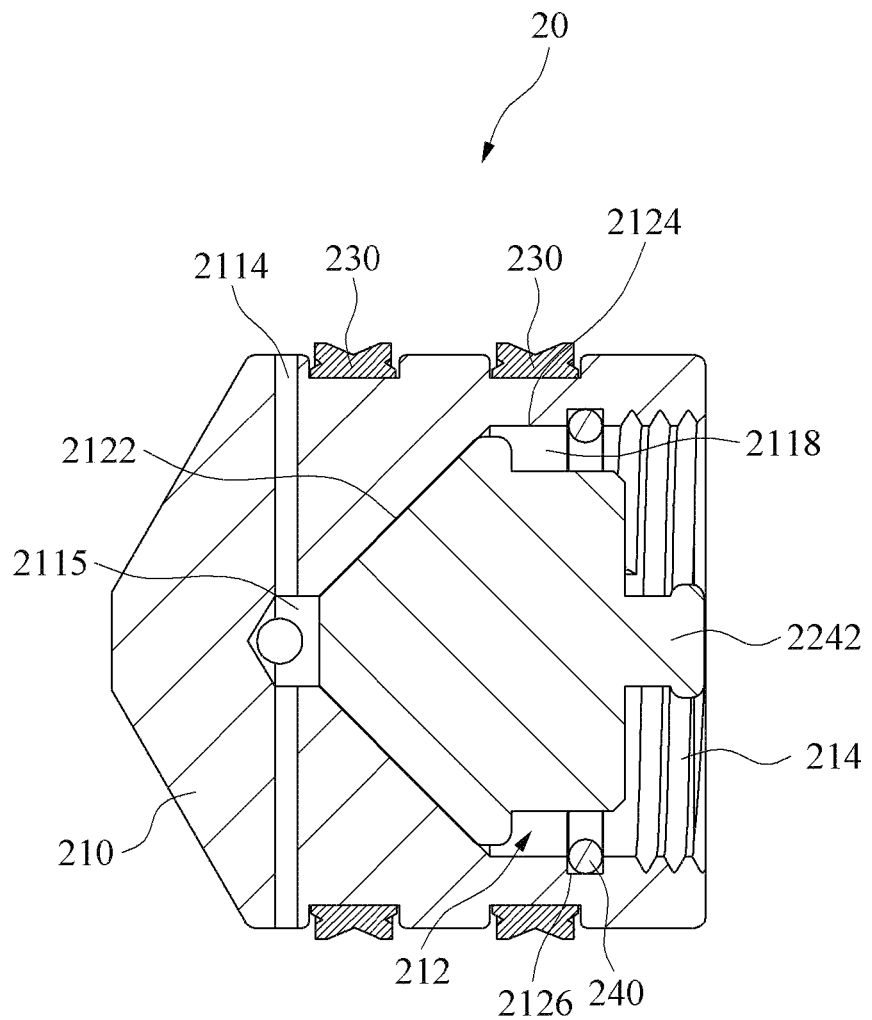
FIG. 6 is a cross-sectional view schematically illustrating a state in which a passage in a piston according to an example embodiment is interrupted.
Figure 7:
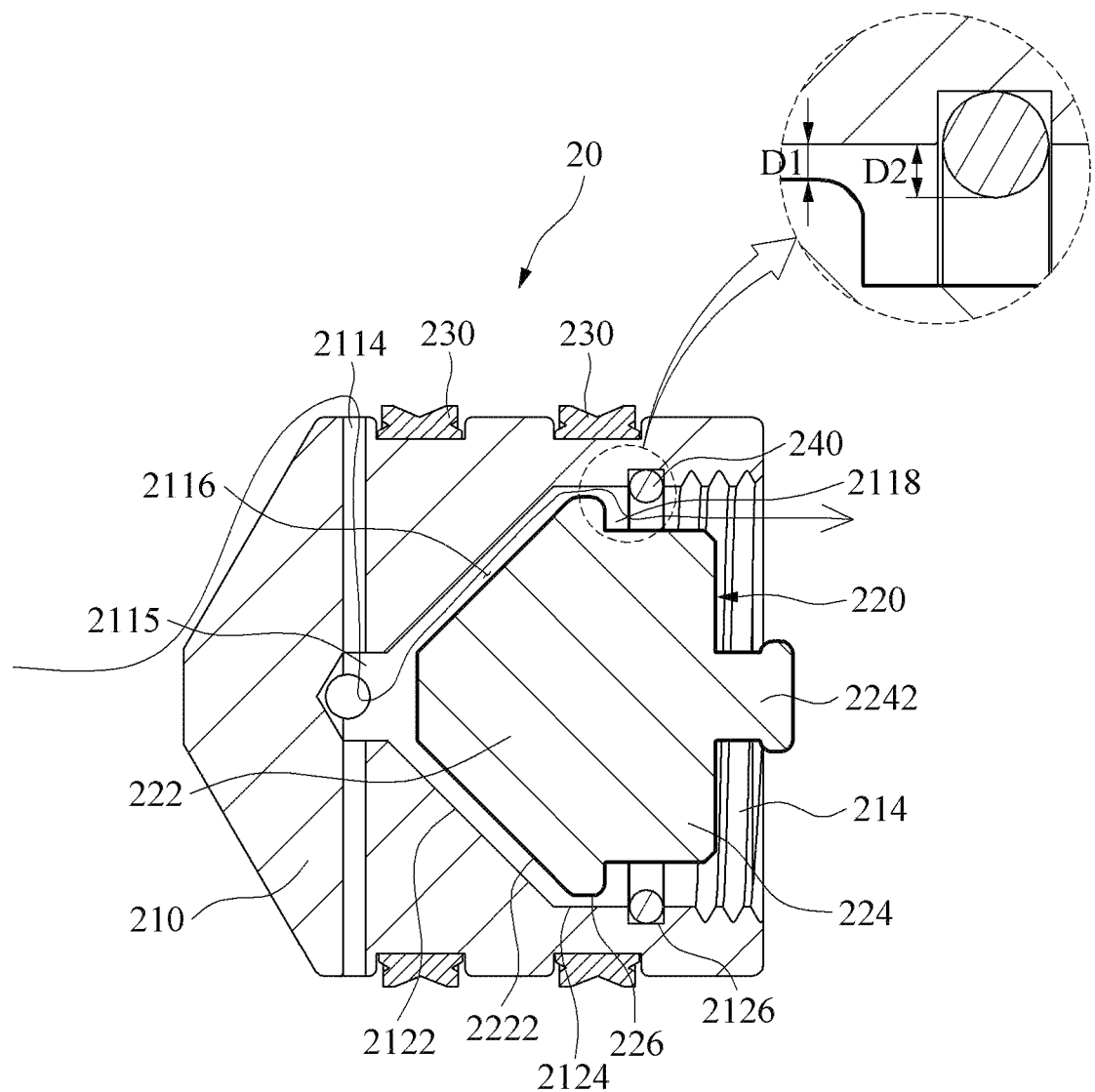
FIG. 7 is a cross-sectional view schematically illustrating a state in which the passage in a piston according to an example embodiment is open.

FIG. 6 is a cross-sectional view schematically illustrating a state in which the passage in the piston according to the example embodiment is interrupted, and FIG. 7 is a cross-sectional view schematically illustrating a state in which the passage in the piston according to the example embodiment is open.

Figure 8:
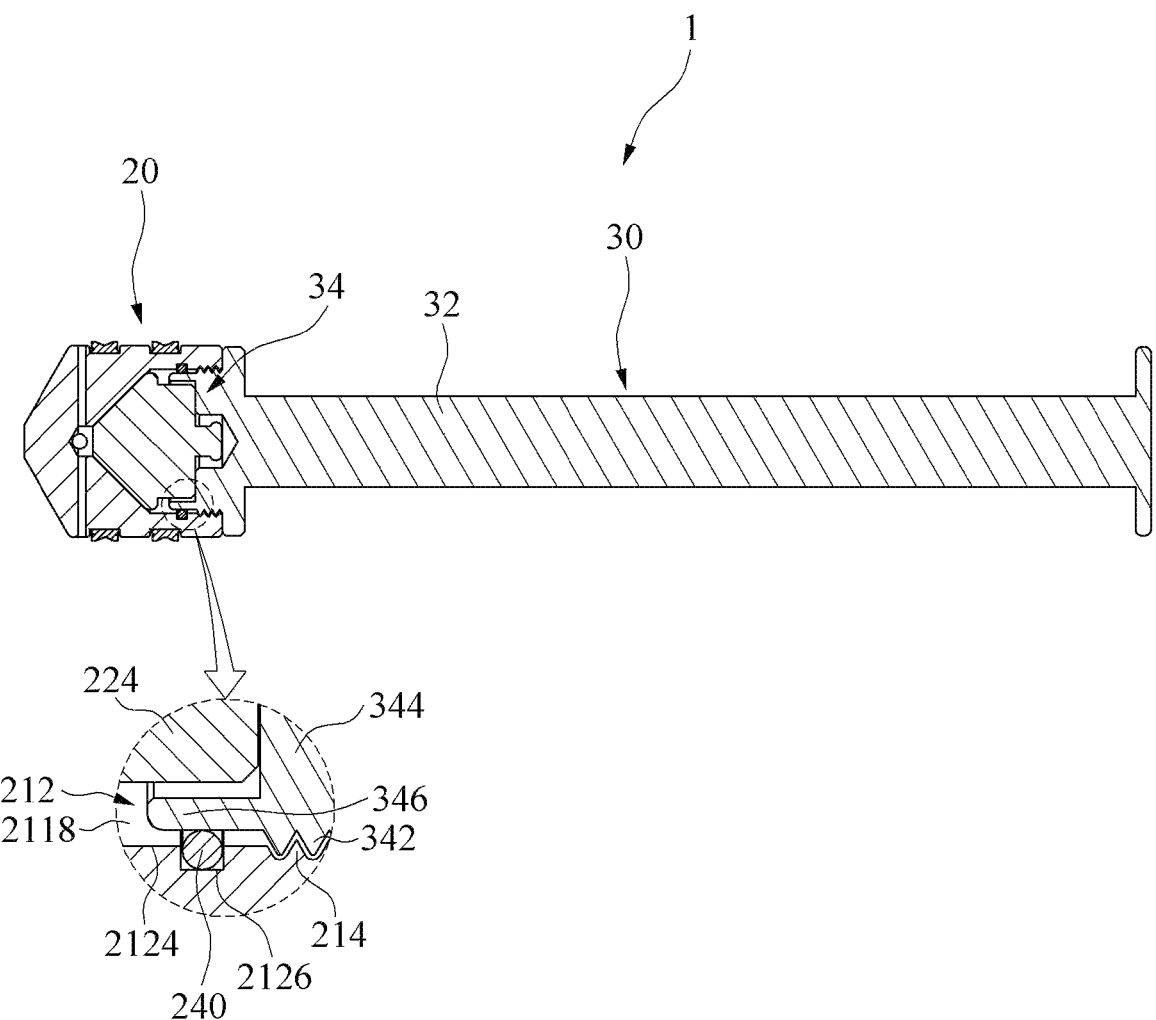
FIG. 8 is a cross-sectional view schematically illustrating a state in which a push rod is coupled to a piston according to an example embodiment.

FIG. 8 is a cross-sectional view schematically illustrating a state in which the push rod is coupled to the piston according to the example embodiment.

Referring to FIGS. 4 to 8, the piston 20 according to the example embodiment may include the piston body 210, the valve 220, the one or more outer sealing members 230, and an inner sealing member 240.

The piston body 210 may have, on the outside thereof, an inlet 2112 through which a material flows in. For example, the oil in the oil layer OL described above with reference to FIG. 3 may enter the piston body 210 through the inlet 2112 and may thereafter flow through the passage defined in the piston body 210. The piston body 210 may have, on the outside thereof, one or more recesses 219 in which the one or more outer sealing members 230 are mounted.

The passage defined in the piston body 210 may have one or more orientations. For example, the passage may include a first path 2114 extending from one side of the piston body 210 to the center of the piston body 210, a second path 2116 extending from the center of the piston body 210 to the back of the piston body 210, and a third path 2118 extending from the back of the piston body 210 to the outside of the piston body 210. The first path 2114 is configured to be in fluid communication with the inlet 2112, the second path 2116 is configured to be selectively in fluid communication with the first path 2114 and the third path 2118, and the third path 2118 is configured to be in fluid communication with the outside of the piston body 210.

In an example embodiment, the passage defined in the piston body 210 may further include a chamber 2115 located between the first path 2114 and the second path 2116. The chamber 2115 may be located in the center of the piston body 210. When fluid communication between the first path 2114 and the third path 2118 through the second path 2116 is interrupted, a material may stay in the chamber 2115. While the valve 220 is contact with a first inner surface 2122 of a receiving portion 212, fluid communication between the chamber 2115 and the second path 2116 may be interrupted.

The piston body 210 may include the receiving portion 212 configured to receive the valve 220. The receiving portion 212 may have inner surfaces in shapes corresponding to the external appearance of the valve 220. For example, the receiving portion 212 may have the first inner surface 2122 tapered along the fore/aft direction of the piston body 210 and a second inner surface 2124 that meets the first inner surface 2122 and that is substantially horizontal along the fore/aft direction of the piston body 210. In an example embodiment, the first inner surface 2122 may have a gradually increasing width from the front to the back of the piston 20.

The piston body 210 may include a piston coupling part 214 configured to be coupled with the push rod 30. For example, the piston coupling part 214 may include a thread formed on the second inner surface 2124 of the receiving portion 212.

The valve 220 may include a front valve part 222 and a rear valve part 224.

The front valve part 222 may be configured to interrupt the passage. The front valve part 222 may be contact with an inner surface of at least a portion of the receiving portion 212. For example, the front valve part 222 may be contact with the first inner surface 2122 of the receiving portion 212. The front valve part 222 may have a shape corresponding to the first inner surface 2122 of the receiving portion 212.

A clearance may be formed between an outer surface 2222 of the front valve part 222 and the first inner surface 2122 of the receiving portion 212. The clearance may be formed when the front valve part 222 is separated from the first inner surface 2122. When the front valve part 222 makes contact with the first inner surface 2122 of the receiving portion 212 as illustrated in FIG. 6, no clearance exists between the outer surface 2222 of the front valve part 222 and the first inner surface 2122 of the receiving portion 212, whereas when the front valve part 222 is separated from the first inner surface 2122 of the receiving portion 212 as illustrated in FIG. 7, a clearance is formed between the outer surface 2222 of the front valve part 222 and the first inner surface 2122 of the receiving portion 212. The clearance may form at least a portion of the second path 2116.

The rear valve part 224 is configured to guide a movement of a material along the passage. The rear valve part 224 may be parallel to an inner surface of at least a portion of the receiving portion 212. For example, the rear valve part 224 may be parallel to the second inner surface 2124 of the receiving portion 212. The rear valve part 224 extends from the front valve part 222 toward the back of the piston body 210.

In an example embodiment, the valve 220 may include a protruding component 226. The protruding component 226 may be formed between the front valve part 222 and the rear valve part 224. The protruding component 226 may protrude toward the inner surfaces of the piston body 210. In an example embodiment, the protruding component 226 may protrude toward the second inner surface 2124 of the receiving portion 212.

In an example embodiment, the valve 220 may include a valve coupling part 2242. The valve coupling part 2242 is configured to be coupled with the push rod 30. For example, the valve coupling part 2242 may have a male engagement formation. The shape of the valve coupling part 2242 may be appropriately set according to the shape of the push rod 30. The valve coupling part 2242 may extend from the rear valve part 224 toward the back of the piston body 210.

The inner sealing member 240 is configured to prevent separation of the valve 220 from the piston body 210. In the passage defined in the piston body 210, the inner sealing member 240 may be provided between the inner surfaces of the piston body 210 and the valve 220. For example, the inner sealing member 240 may be provided on the second inner surface 2124 of the receiving portion 212 on the third path 2128.

In an example embodiment, the inner sealing member 240 is configured such that the protruding component 226 is stopped by the inner sealing member 240. The inner sealing member 240 may have a ring shape. For example, the distance D1 between the second inner surface 2124 of the receiving portion 212 and the protruding component 226 may be smaller than the distance D2 from the second inner surface 2124 of the receiving portion 212 to the inside of the inner sealing member 240.

In an example embodiment, a portion of the inner sealing member 240 may be embedded in the piston body 210. For example, the receiving portion 212 may include a groove 2126 configured to receive a portion of the inner sealing member 240. The groove 2126 may be formed on the second inner surface 2124.

According to the structure described above, the inner sealing member 240 prevents the valve 220 from being separated from the piston body 210 when the valve 220 is about to escape from the piston body 210 before the push rod 30 is coupled with the piston body 210 and the valve 220.

The push rod 30 is coupled with the piston body 210 and the valve 220 and is configured to fix the valve 220 to the piston body 210 to interrupt the passage defined in the piston body 210. In an example embodiment, the push rod 30 may include a first push rod coupling part 342 configured to be coupled with the piston coupling part 214 and a second push rod coupling part 344 located inward of the first push rod coupling part 342 and coupled with the valve coupling part 2242 while facing the rear valve part 224 and surrounding the valve coupling part 2242. For example, the first push rod coupling part 342 may have a thread shape.

When the push rod 30 is coupled with the piston body 210 and the valve 220, a portion of the push rod 30 may interrupt the passage while making contact with the inner sealing member 240. For example, the push rod 30 may include a sealing forming part 346. The sealing forming part 346 may make contact with the inner sealing member 240 while filling at least a portion of a space between the piston body 210 and the valve 220. Accordingly, the sealing forming part 346 may interrupt communication of the passage together with the first push rod coupling part 342 and the second push rod coupling part 344. In an example embodiment, the sealing forming part 346 may form sealing of the third path 2118 between the second inner surface 2124 of the receiving portion 212 and the rear valve part 224.

The contact between the sealing forming part 346 and the inner sealing member 240 is constantly made until the push rod 30 is separated from the piston body 210 together with the valve 220 after the push rod 30 is coupled with the piston body 210 and the valve 220. While the sealing forming part 346 makes contact with the inner sealing member 240, the inner sealing member 240 may be elastically deformed, or may remain deformed.

While the example embodiments have been described above with reference to the limited drawings, it will be understood by those skilled in the art that various modifications and alterations can be made without departing from the spirit and scope of the present invention. For example, suitable results may be achieved even if the described techniques are performed in a different order, and/or the described components such as a system, a structure, a device, a circuit, and the like are coupled or combined in a different manner or replaced or supplemented by other components or their equivalents.

The invention claimed is:

1. A piston for centrifugation, comprising:
a piston body having a passage defined therein, the passage extending from a front to a rear of the piston, and materials at the front of the piston being movable to the rear of the piston through the passage; and
a valve disposed in the passage to selectively open or interrupt the passage,
wherein the piston body comprises a receiving portion configured to receive the valve and form a portion of the passage, and wherein the receiving portion has an inner surface in a shape corresponding to at least a portion of the valve,
wherein the valve is configured to move between a first position in which the valve is contact with the inner surface and the passage is interrupted, and a second position in which the valve is separated from the inner surface of the receiving portion and the passage is open,
wherein during the centrifugation that involves application of a centrifugal force to the piston, the valve is configured to move from the second position to the first position and interrupt the passage such that the materials at the front of the piston are centrifugally separated, and when an external force is applied to the piston while a centrifugal force is not applied to the piston, the valve is configured to freely move relative to the piston body from the first position to the second position and open the passage such that at least a portion of the materials at the front of the piston are movable to the rear of the piston.

2. The piston of claim 1, wherein the center of rotation of the centrifugal force is located at the rear of the piston body, wherein the piston body is located inside a container that receives the piston, and
wherein the piston body applies pressure to the materials at the front of the piston while moving along an inside of the container depending on the external force.

3. The piston of claim 1, wherein the passage includes:
a first path extending from one side of the piston body to a center of the piston body; and
a second path extending from the center of the piston body to the rear of the piston body, and
wherein the second path includes a clearance formed between the valve and the inner surface when the valve is separated from the inner surface.

4. The piston of claim 1, wherein a portion of the receiving portion having the inner surface has a decreasing width toward the front of the piston in a lengthwise direction of the piston body.

5. A centrifugal separator comprising:
a piston including a piston body having a passage defined therein, the passage extending from the front to the rear of the piston, a valve disposed in the passage, and a sealing member located on the passage and provided between the piston body and the valve; and
a push rod to fix the valve to the piston body to interrupt the passage, the push rod being coupled with the piston body and the valve,
wherein the push rod is configured to be contact with the sealing member and interrupt communication of the passage together with the sealing member when the push rod is coupled with the piston body and the valve in a state in which a centrifugation is completed, with no centrifugal force applied to the piston.

6. The centrifugal separator of claim 5, wherein a portion of the push rod is disposed inside the piston body to fill a space between the piston body and the valve and forms sealing of the passage together with the sealing member.

7. The centrifugal separator of claim 5, wherein the sealing member prevents separation of the valve from the piston body before the push rod is coupled with the piston body and the valve, and
wherein the sealing member is elastically deformed before the push rod is separated from the piston body together with the valve after coupled with the piston body and the valve.

8. The centrifugal separator of claim 5, wherein the piston further includes a groove, a portion of the sealing member being embedded in the piston body through the groove.

9. A centrifugation method for separating bio-materials using a piston for centrifugation,
wherein the piston includes a piston body having a passage defined therein and a valve disposed in the passage to open or interrupt the passage, the passage extending from the front to the rear of the piston, and the bio-materials being movable through the passage,
wherein with respect to a container that receives the piston and the bio-materials, the bio-materials are located at the front of the piston body, and a center of rotation of a centrifugal force is located behind the piston body, and
wherein the centrifugation method comprises:
separating the bio-materials at the front of the piston body into layers in a direction away from the front of the piston body with respect to the center of rotation in a state in which the valve interrupts the passage while the centrifugal force is applied to the piston;
releasing the centrifugal force applied to the piston, connecting a push rod to the piston body, and removing a bio-material farthest away from the piston body among the bio-materials from the container by applying pressure to the bio-materials by pushing the piston body in a direction toward the front of the piston body;
moving a bio-material closest to the piston body among the bio-materials to the rear of the piston body through the passage in a state in which the valve moves freely relative to the piston body and opens the passage, by applying pressure to the bio-materials at the front of the piston by pushing the piston with the push rod in a state in which the connection of the push rod to the piston body is released; and
obtaining at least one type of remaining bio-materials.

* * * * *